US009005551B2

(12) United States Patent
Chen et al.

(10) Patent No.: US 9,005,551 B2
(45) Date of Patent: Apr. 14, 2015

(54) SAMPLE VESSELS

(75) Inventors: Shuqi Chen, Framingham, MA (US);
Lingjun Chen, Framingham, MA (US)

(73) Assignee: Roche Molecular Systems, Inc.,
Pleasanton, CA (US)

(*) Notice: Subject to any disclaimer, the term of this patent is extended or adjusted under 35 U.S.C. 154(b) by 1073 days.

(21) Appl. No.: 13/022,311

(22) Filed: Feb. 7, 2011

(65) Prior Publication Data
US 2011/0143968 A1 Jun. 16, 2011

Related U.S. Application Data

(60) Division of application No. 11/740,650, filed on Apr. 26, 2007, now abandoned, which is a continuation of application No. 10/241,816, filed on Sep. 11, 2002, now Pat. No. 7,799,521.

(60) Provisional application No. 60/318,768, filed on Sep. 11, 2001.

(51) Int. Cl.
*B01L 3/14* (2006.01)
*B01L 3/00* (2006.01)
(Continued)

(52) U.S. Cl.
CPC ........... *B01L 3/50825* (2013.01); *A61B 5/1427* (2013.01); *A61B 5/1438* (2013.01); *B01L 3/502* (2013.01); *B01L 3/5027* (2013.01); *B01L 3/505* (2013.01); *B01L 2200/026* (2013.01); *B01L 2300/021* (2013.01); *B01L 2300/046* (2013.01);
(Continued)

(58) Field of Classification Search
CPC ............................ B01L 3/5027; B04B 5/0428
See application file for complete search history.

(56) References Cited

U.S. PATENT DOCUMENTS 2,895,475 A 7/1959 Cole
3,036,894 A * 5/1962 Forestiere ..................... 436/165
(Continued)

FOREIGN PATENT DOCUMENTS

CA 2632856 * 12/1999 ............. G01N 37/00
DE 2007405 10/1970
(Continued)

OTHER PUBLICATIONS

Alon, et al, "The Kinetics of L-selectin Tethers and the Mechanics of Selectin-mediated Rolling,", J. Cell Biol., 138 (5); 1169-1180 (1997).
(Continued)

*Primary Examiner* — Jill Warden
*Assistant Examiner* — Timothy G Kingan
(74) *Attorney, Agent, or Firm* — Jeffery P. Bernhardt

(57) ABSTRACT

A sample vessel may include a segmented tubule and an interface receiving the tubule. The segmented tubule may include an opening for receiving a sample material and at least one compressible section, the at least one compressible section having a wall constructed at least partially from a material having sufficient flexibility to permit compression of opposed sections of the wall into contact with one another, and at least two segments of the tubule being fluidically isolated from one another by a bonding of a fluid-tight seal between opposed sections of the tubule wall, wherein said fluid-tight seal irreversibly opens upon application of fluid pressure greater than a threshold value to permit selective fluid communication between the opposed sections. The interface may facilitate delivery of a sample material to the tubule through the opening.

24 Claims, 7 Drawing Sheets

(51) Int. Cl.
*A61B 5/155* (2006.01)
*A61B 5/15* (2006.01)

(52) U.S. Cl.
CPC .... *B01L 2300/047* (2013.01); *B01L 2300/0636* (2013.01); *B01L 2300/0816* (2013.01); *B01L 2300/0887* (2013.01); *B01L 2400/0481* (2013.01); *B01L 2400/0655* (2013.01)

(56) References Cited

U.S. PATENT DOCUMENTS

| | | | |
|---|---|---|---|
| 3,276,447 A * | 10/1966 | Hamilton | 604/403 |
| 3,441,205 A | 4/1969 | Young, Jr. | |
| 3,545,671 A * | 12/1970 | Ross | 422/44 |
| 3,556,731 A | 1/1971 | Martin | |
| 3,561,186 A * | 2/1971 | Pickering | 53/416 |
| 3,579,303 A | 5/1971 | Pickering | |
| 3,607,097 A | 9/1971 | Auphan et al. | |
| 3,620,678 A | 11/1971 | Guigan et al. | |
| 3,697,227 A | 10/1972 | Goldstein et al. | |
| 3,698,822 A | 10/1972 | Polanyi | |
| 3,736,933 A | 6/1973 | Szabo | |
| 3,819,158 A | 6/1974 | Sharpe et al. | |
| 3,888,629 A | 6/1975 | Bagshawe et al. | |
| 3,918,913 A | 11/1975 | Stevenson et al. | |
| 4,038,030 A | 7/1977 | Albright et al. | |
| 4,065,263 A | 12/1977 | Woodbridge, III | |
| RE29,725 E | 8/1978 | Johnson et al. | |
| 4,166,457 A | 9/1979 | Jacobsen et al. | |
| 4,187,861 A | 2/1980 | Heffernan | |
| 4,267,149 A | 5/1981 | Bruckner et al. | |
| 4,329,698 A | 5/1982 | Smith | |
| 4,426,451 A | 1/1984 | Columbus | |
| 4,430,139 A | 2/1984 | Baverstock et al. | |
| 4,446,232 A | 5/1984 | Liotta | |
| 4,472,498 A | 9/1984 | Masuda et al. | |
| 4,596,271 A | 6/1986 | Brundage | |
| 4,608,275 A | 8/1986 | Kukanskis et al. | |
| 4,695,430 A | 9/1987 | Coville et al. | |
| 4,752,449 A | 6/1988 | Jackson et al. | |
| 4,803,154 A | 2/1989 | Uo et al. | |
| 4,820,297 A | 4/1989 | Kaufman et al. | |
| 4,822,568 A | 4/1989 | Tomita et al. | |
| 4,846,005 A | 7/1989 | Bacehowski et al. | |
| 4,900,321 A | 2/1990 | Kaufman et al. | |
| 4,903,708 A * | 2/1990 | Saint-Amand | 600/562 |
| 4,917,864 A | 4/1990 | Marsoner et al. | |
| 5,019,348 A | 5/1991 | Ohms et al. | |
| 5,057,438 A | 10/1991 | Imai et al. | |
| 5,061,445 A | 10/1991 | Zoski et al. | |
| 5,073,484 A | 12/1991 | Swanson et al. | |
| 5,087,425 A | 2/1992 | Flossdorf et al. | |
| 5,089,233 A | 2/1992 | DeVaney, Jr. et al. | |
| 5,098,660 A | 3/1992 | Devaney, Jr. | |
| 5,120,662 A | 6/1992 | Chan et al. | |
| 5,133,938 A * | 7/1992 | Glanville et al. | 422/537 |
| 5,143,084 A | 9/1992 | Macemon et al. | |
| 5,176,203 A | 1/1993 | Larzul et al. | |
| 5,178,832 A | 1/1993 | Phillips et al. | |
| 5,185,127 A | 2/1993 | Vonk | |
| 5,187,084 A | 2/1993 | Hallsby | |
| 5,229,297 A | 7/1993 | Schnipelsky et al. | |
| 5,244,813 A | 9/1993 | Walt et al. | |
| 5,258,314 A | 11/1993 | Skerratt et al. | |
| 5,270,183 A | 12/1993 | Corbett et al. | |
| 5,356,785 A | 10/1994 | McMahon et al. | |
| 5,374,395 A | 12/1994 | Robinson et al. | |
| 5,380,665 A | 1/1995 | Cusack et al. | |
| 5,391,478 A | 2/1995 | Greene et al. | |
| 5,422,271 A | 6/1995 | Chen et al. | |
| 5,424,220 A | 6/1995 | Goerlach-Graw et al. | |
| 5,430,957 A | 7/1995 | Eigen et al. | |
| 5,455,175 A | 10/1995 | Wittwer et al. | |
| 5,460,780 A | 10/1995 | Devaney, Jr. et al. | |
| 5,475,610 A | 12/1995 | Atwood et al. | |
| 5,491,067 A | 2/1996 | Setcavage et al. | |
| 5,504,007 A | 4/1996 | Haynes | |
| 5,508,197 A | 4/1996 | Hansen et al. | |
| 5,567,617 A | 10/1996 | Caprio et al. | |
| 5,571,410 A | 11/1996 | Swedberg et al. | |
| 5,576,218 A | 11/1996 | Zurek et al. | |
| 5,591,573 A | 1/1997 | Whalen et al. | |
| 5,602,756 A | 2/1997 | Atwood et al. | |
| 5,626,732 A | 5/1997 | Allington | |
| 5,631,683 A | 5/1997 | Nishioka et al. | |
| 5,656,501 A | 8/1997 | Yedgar et al. | |
| 5,668,330 A | 9/1997 | Bartlett-Hooker et al. | |
| 5,709,668 A | 1/1998 | Wacks | |
| 5,714,380 A | 2/1998 | Neri et al. | |
| 5,735,824 A | 4/1998 | Hjertman et al. | |
| 5,736,106 A | 4/1998 | Ishiguro et al. | |
| 5,780,222 A | 7/1998 | Peddada et al. | |
| 5,795,547 A | 8/1998 | Moser et al. | |
| 5,801,052 A | 9/1998 | Bartlett-Hooker et al. | |
| 5,810,778 A | 9/1998 | Hjertman et al. | |
| 5,827,480 A | 10/1998 | Haff et al. | |
| 5,830,411 A | 11/1998 | Martinell Gisper-Sauch et al. | |
| 5,847,734 A | 12/1998 | Pawlowski, Jr. | |
| 5,863,502 A | 1/1999 | Southgate et al. | |
| 5,866,366 A | 2/1999 | Kallender | |
| 5,897,842 A | 4/1999 | Dunn et al. | |
| 5,942,432 A | 8/1999 | Smith et al. | |
| 5,985,651 A | 11/1999 | Hunicke-Smith | |
| 6,016,683 A | 1/2000 | Betts et al. | |
| 6,019,945 A | 2/2000 | Ohishi et al. | |
| 6,033,880 A | 3/2000 | Haff et al. | |
| 6,066,296 A | 5/2000 | Brady et al. | |
| 6,068,751 A | 5/2000 | Neukermans | |
| 6,159,727 A | 12/2000 | Bochkariov | |
| 6,163,714 A | 12/2000 | Stanley et al. | |
| 6,174,670 B1 | 1/2001 | Wittwer et al. | |
| 6,180,698 B1 | 1/2001 | Porter et al. | |
| 6,186,982 B1 | 2/2001 | Gross et al. | |
| 6,190,416 B1 | 2/2001 | Choteau et al. | |
| 6,194,160 B1 | 2/2001 | Levin | |
| 6,210,036 B1 | 4/2001 | Eberle et al. | |
| 6,210,369 B1 | 4/2001 | Wilmot et al. | |
| 6,210,958 B1 | 4/2001 | Brust et al. | |
| 6,250,166 B1 | 6/2001 | Dingwell et al. | |
| 6,251,660 B1 | 6/2001 | Muir et al. | |
| 6,264,892 B1 | 7/2001 | Kaltenbach et al. | |
| 6,274,726 B1 | 8/2001 | Laugharn, Jr. et al. | |
| 6,290,960 B1 | 9/2001 | Kink et al. | |
| 6,299,601 B1 | 10/2001 | Hjertman | |
| 6,300,138 B1 | 10/2001 | Gleason et al. | |
| 6,300,308 B1 | 10/2001 | Schroit | |
| 6,303,083 B1 | 10/2001 | Johnson et al. | |
| 6,318,191 B1 | 11/2001 | Chen | |
| 6,439,759 B1 | 8/2002 | Ray et al. | |
| 6,440,072 B1 | 8/2002 | Schuman et al. | |
| 6,440,725 B1 | 8/2002 | Pourahmadi et al. | |
| 6,748,332 B2 | 6/2004 | Chen | |
| 6,780,617 B2 | 8/2004 | Chen | |
| 6,964,862 B2 | 11/2005 | Chen | |
| 7,337,072 B2 | 2/2008 | Chen | |
| 7,718,421 B2 | 5/2010 | Chen et al. | |
| 7,785,535 B2 | 8/2010 | Chen et al. | |
| 7,799,521 B2 | 9/2010 | Chen | |
| 7,833,489 B2 | 11/2010 | Chen | |
| 2002/0049557 A1 | 4/2002 | Chen | |
| 2002/0064484 A1 | 5/2002 | Lin et al. | |
| 2003/0049833 A1 | 3/2003 | Chen et al. | |
| 2003/0208105 A1 | 11/2003 | Newman et al. | |
| 2004/0105782 A1 | 6/2004 | Chen | |
| 2004/0161788 A1 | 8/2004 | Chen et al. | |
| 2004/0209331 A1 | 10/2004 | Ririe | |
| 2004/0223878 A1 | 11/2004 | Chen | |
| 2005/0019875 A1 | 1/2005 | Chen | |
| 2006/0154341 A1 | 7/2006 | Chen | |
| 2008/0003564 A1 | 1/2008 | Chen et al. | |
| 2008/0038813 A1 | 2/2008 | Chen | |

(56) References Cited

U.S. PATENT DOCUMENTS

| | | | |
|---|---|---|---|
| 2010/0159532 A1* | 6/2010 | Colpan et al. | 435/91.5 |
| 2010/0218621 A1 | 9/2010 | Chen et al. | |

FOREIGN PATENT DOCUMENTS

| | | |
|---|---|---|
| DE | 2753865 | 6/1979 |
| EP | 0047806 | 3/1982 |
| EP | 0047806 A1 | 3/1982 |
| EP | 0139373 | 5/1985 |
| EP | 0312394 | 4/1989 |
| EP | 0312394 A2 | 4/1989 |
| EP | 0381501 A2 | 8/1990 |
| EP | 0435380 | 7/1991 |
| EP | 0488769 A2 | 6/1992 |
| EP | 0488769 A2 | 6/1992 |
| EP | 0504772 A2 | 9/1992 |
| EP | 0504772 A2 | 9/1992 |
| EP | 0739241 | 10/1996 |
| EP | 0955097 | 11/1999 |
| EP | 1000661 | 5/2000 |
| EP | 1106250 | 6/2001 |
| FR | 1513306 | 2/1968 |
| FR | 1513306 A | 2/1968 |
| FR | 2590673 | 5/1987 |
| FR | 2590673 A1 | 5/1987 |
| FR | 2672231 | 8/1992 |
| WO | WO80/02106 * | 10/1980 |
| WO | 9420831 | 9/1994 |
| WO | WO-94/20831 A1 | 9/1994 |
| WO | WO-94/26414 A1 | 11/1994 |
| WO | 9727324 | 7/1997 |
| WO | WO-97/27324 | 7/1997 |
| WO | 9740939 | 11/1997 |
| WO | WO-97/40939 | 11/1997 |
| WO | 9748818 | 12/1997 |
| WO | WO-97/48818 | 12/1997 |
| WO | 9809728 | 3/1998 |
| WO | WO-98/09728 A1 | 3/1998 |
| WO | 9816313 | 4/1998 |
| WO | WO-98/16313 A1 | 4/1998 |
| WO | 9843740 | 10/1998 |
| WO | WO-98/43740 | 10/1998 |
| WO | 9850147 | 11/1998 |
| WO | WO-98/50147 | 11/1998 |
| WO | 9926724 | 6/1999 |
| WO | WO-99/26724 | 6/1999 |
| WO | 9967646 A1 | 12/1999 |
| WO | 9967647 | 12/1999 |
| WO | WO-99/67646 A1 | 12/1999 |
| WO | WO-99/67647 | 12/1999 |
| WO | 0013014 | 3/2000 |
| WO | WO-00/13014 | 3/2000 |
| WO | 0023803 A1 | 4/2000 |
| WO | WO-00/23803 A1 | 4/2000 |
| WO | 0025920 | 5/2000 |
| WO | WO-00/25920 | 5/2000 |
| WO | 0107892 A1 | 2/2001 |
| WO | WO-01/07892 A1 | 2/2001 |
| WO | 03007677 | 1/2003 |
| WO | WO-03/007677 | 1/2003 |

OTHER PUBLICATIONS

Belgrader, P., et al., PCR Detection of Bacteria in Seven Minutes, Science 284, pp. 449-450. Apr. 16, 1999.
Ben-Hur et al., "Photodynamic Treatment of Red Blood Cell Concentrates for Virus Inactivation Enhances Red Blood Cell Aggregation: Protection with Antioxidants," Photochem. and Photobiol., 66(4):509-512 (1997).
Boehringer Mannheim, Lightcycler Instrument, pp. 1-16, Jul. 1998.
Chen, et al., "Enhanced aggregability of red blood cells of ss-thalassemia major patients," Am. Physiol. Soc., H1951-1956 (1996).
Chen, et al., "Monitoring of Erythrocyte Aggregate Morphology Under Flow by Computerized Image Analysis," Biorheology, 32(4):498-496 (1995).
Chen, et al., "Monitoring of Red Blood Cell Aggregability in a Flow-Chamber by Computerized Image Analysis," Clin. Hemorheology, 14(4): 497-507 (1994).
Chen, et al., "Red blood cell aggregability is enhanced by physiological levels of hydrostatic pressure", Biochimica et Biophysica Acta 1192, Elsevier Science B.V., 247-252 (1994).
Chen, et al., "Rolling and transient tethering of leukocytes on antibodies reveal specializations of selectins," Proc. Natl. Acad. Sci. USA 94:3172-3177 (1997).
Findlay et all., "Automated Closed-Vessel System . . . " Nov. 9, 1993, pp. 1927-1933.
Intergen, Amplifluor Universal Detection System, Versatile, Quantitative Detection for PCR in Endpoint and Real-time (2001).
International Search Report for PCT/US1999/14105 dated Oct. 19, 1999.
International Search Report for PCT/US2001/49707 dated Jul. 8, 2003.
International Search Report for PCT/US2002/28951 dated Jul. 16, 2002.
Kenneth Mason Publications; "PCR Processor", Research Disclosure, Hampshire, GB, vol. 396 pp. 207-211, (Apr. 1, 1997).
Kenneth Mason Publications; "Simplified PCR Processor and Method", Research Disclosure, Hampshire, GB, vol. 401, pp. 651-655, (Sep. 1, 1997).
Kopp, et al. "Chemical Amplification: Continuous-Flow PCR on a Chip," Science, vol. 280, May 15, 1998.
Rasmussen, et al. "Quantitative PCR by Continuous Fluorescense Monitoring of a Double Strand DNA Specific Binding Dye," Biochemica, No. 2 (1998), pp. 8-11.
Roche Molecular Biochemicals, LightCycler System, Real-time PCR—as flexible as you are, pp. 1-34, Jan. 2000.
Schober, al. et al "Multichannel PCR and Serial Transfer Machine as a Future Tool in Evolutionary Biotechnology," Biotechinques 1995, 18:652-661.
Taylor, et al., "Enhanced Human Red Blood Cell Aggregation While Diving," Naval Medical Research Institute, Bethesda, MD and Dept. of Biochemistry, Hebrew University—Hadasseh Medical School, Jerusalem, Israel (1997).
Wittwer, et al. "Minimizing the Time Required for DNA Amplification by Efficient Heat Transfer to Small Samples," Anal Biochem 1990, 186:328-331.
World Wide Web Page, Nalge Nunc International, DIAPOPS, http://nunc.nalgenunc.com/resource/technical/nag/dp0014.htm, pp. 1-4, Oct. 31, 2000.
World Wide Web Page, Quantitation of DNA/RNA Using Real-time PCR Detection, www.appliedbiosystems.com/molecularbiology/about/white.htm/per/sds/ (Applied Biosystems), pp. 1-8, Oct. 31, 2000.
World Wide Web Page, Quantitative Real-Time PCR, www.lsc.psu.edu/stf/naf/quantitative.htm/ (PennState Life Sciences Consortium, Shared Technology Facilities), pp. 1-3, Oct. 31, 2000.
European Search Report in EP02775793, mailed Sep. 17, 2009.
Chen, et al., "Enhanced aggregability of red blood cells of R-thalassemia major patients," Am. Physiol. Soc., H1951-1956 (1996).
Schober, et al. "Multichannel PCR and Serial Transfer Machine as a Future Tool in Evolutionary Biotechnology," Biotechinques 1995, 18:652-661.
Examination Report for EP 02775793.9 dated Aug. 30, 2011.
Examination Report for EP 04737303.0 dated Jun. 25, 2012.
European Search Report for EP 12194999.4 dated Feb. 28, 2013.
European Examination Report for EP 04737303.0 dated Mar. 4, 2013.
International Search Report for PCT/US2001/49707 dated Jul. 16, 2002.
International Search Report for PCT/US2002/28951 dated Jul. 17, 2003.

* cited by examiner

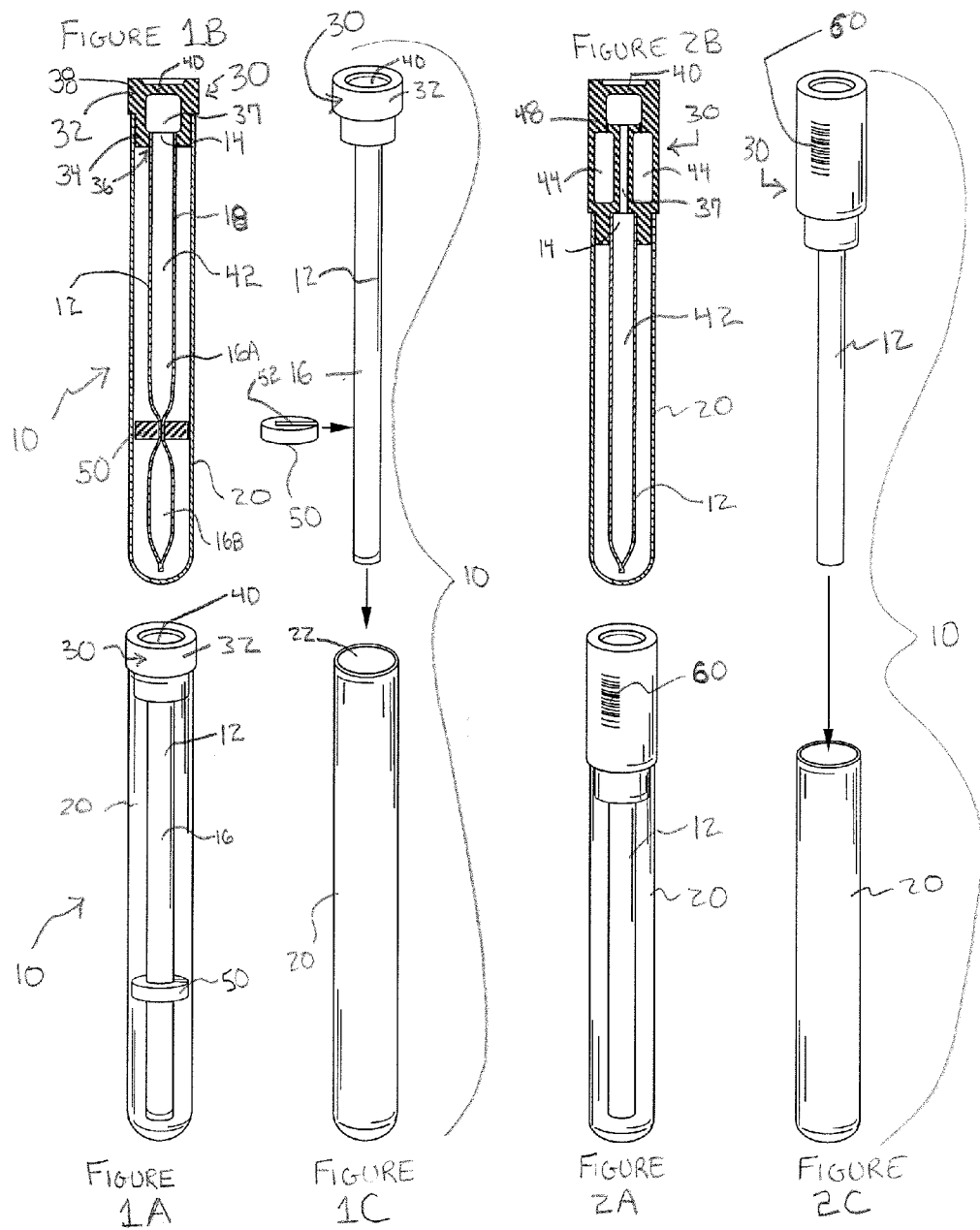

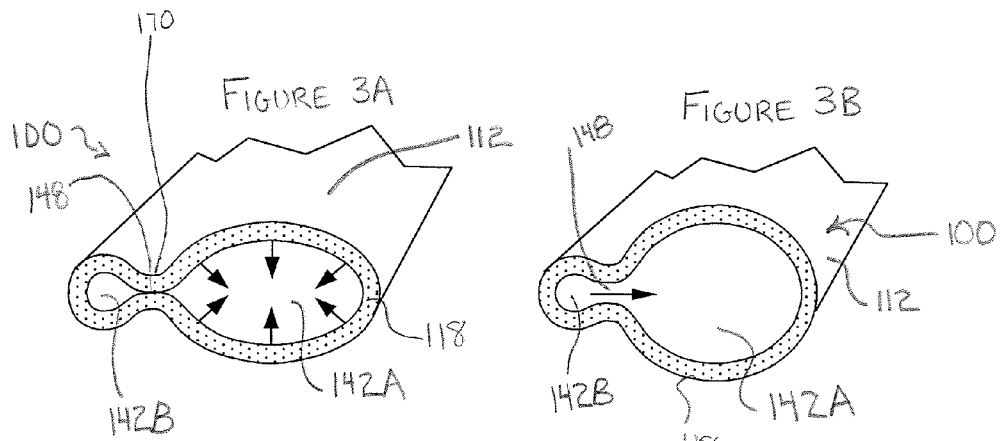
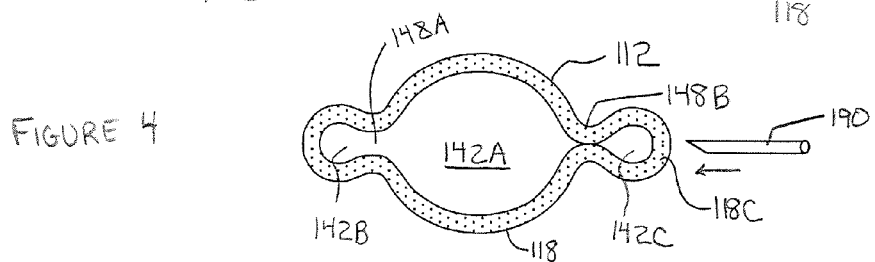
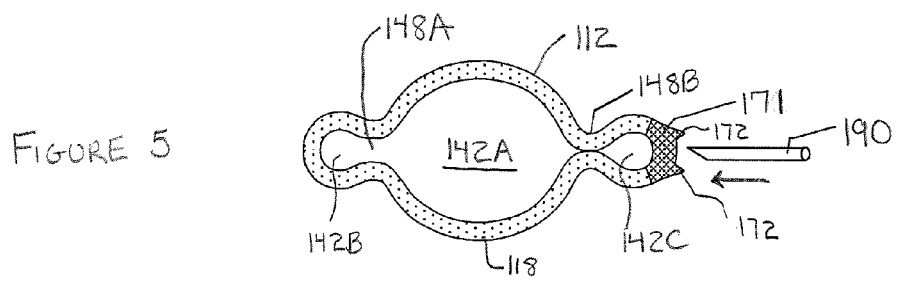
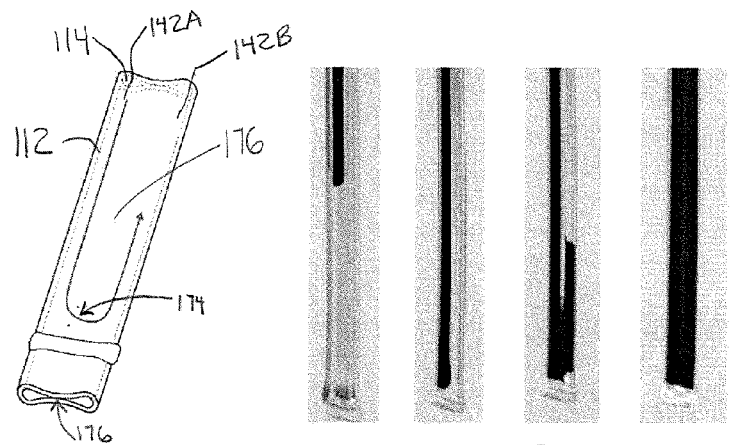

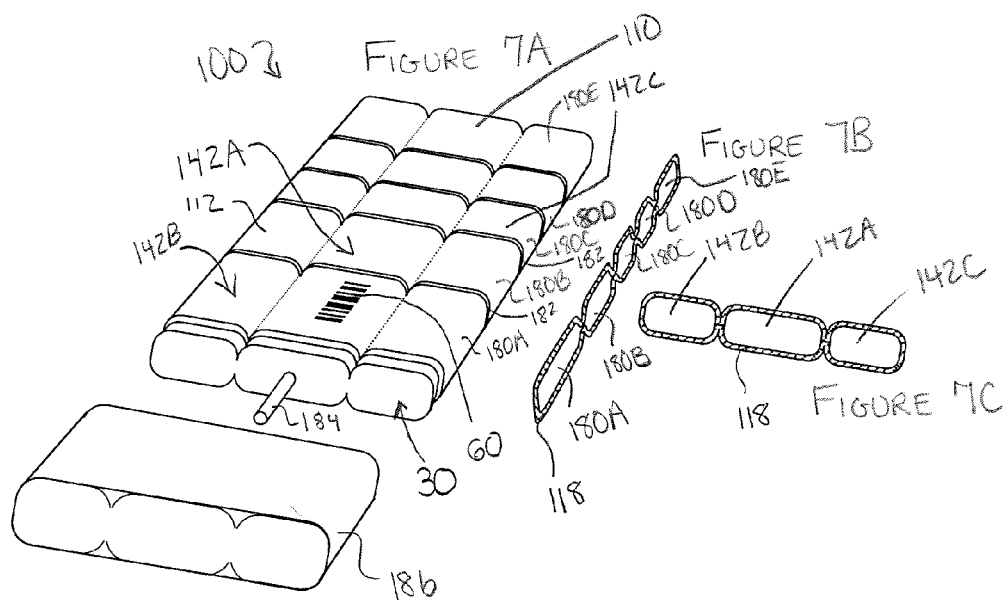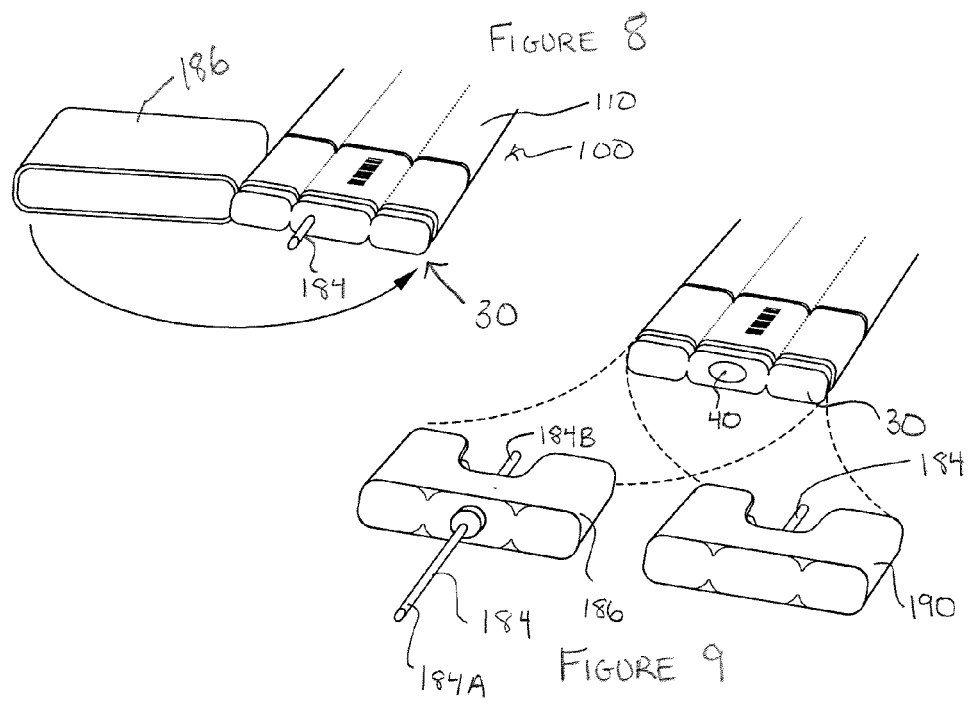

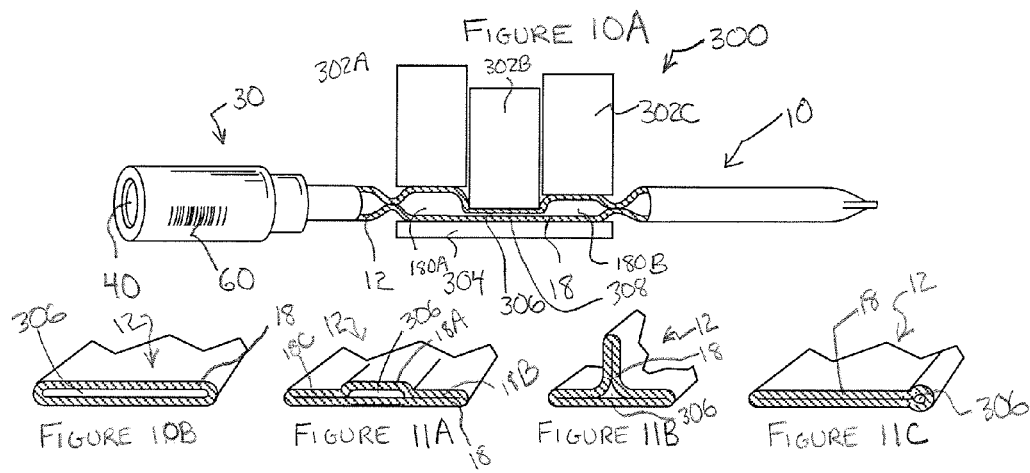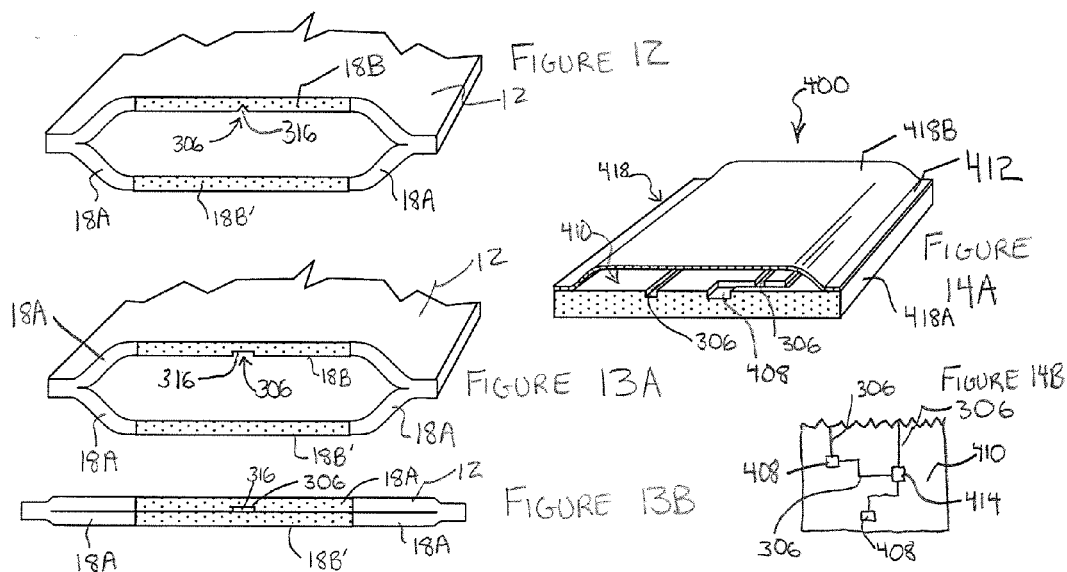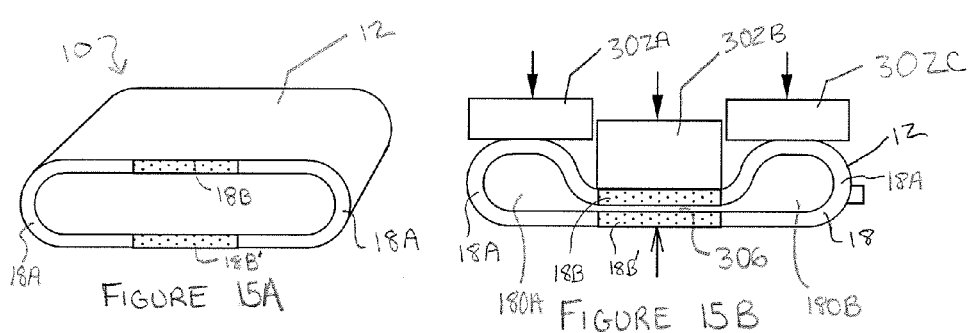

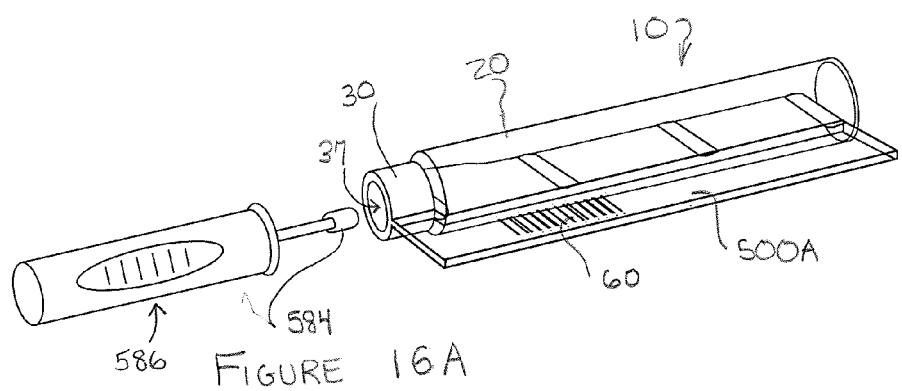
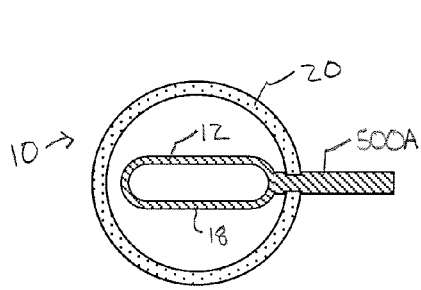
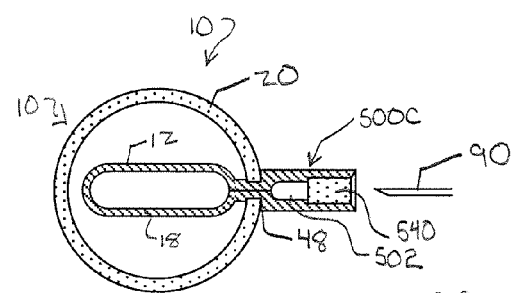
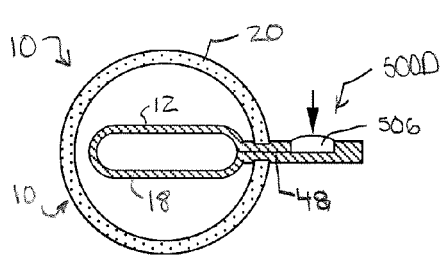
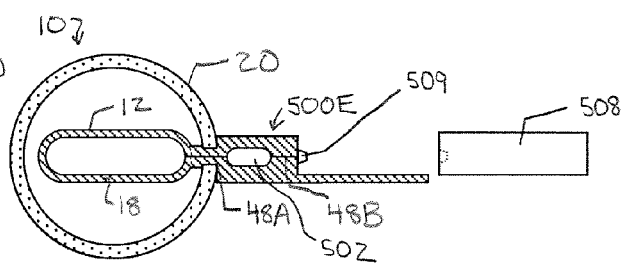

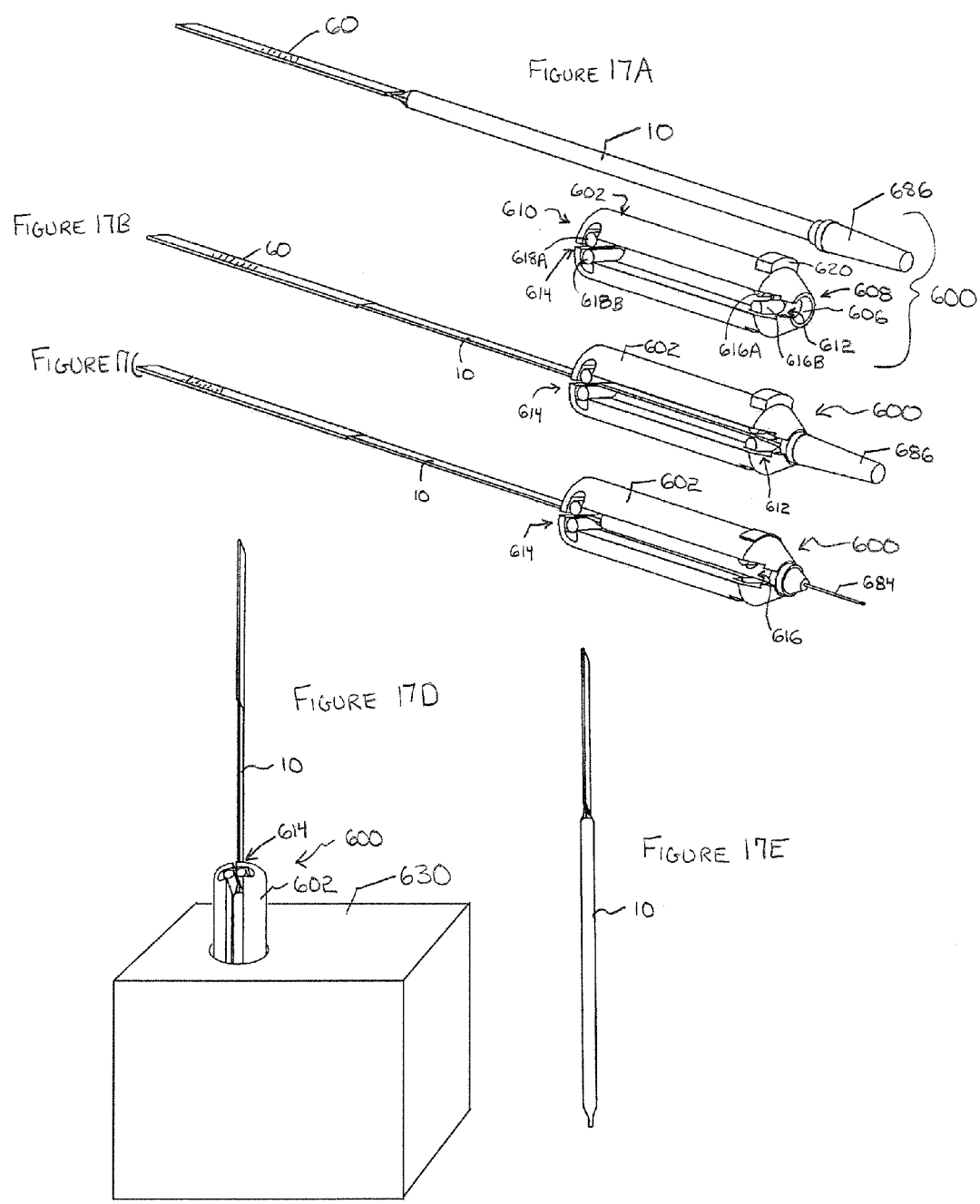

SAMPLE VESSELS

CROSS-REFERENCE TO RELATED APPLICATIONS

This application is a division of U.S. application Ser. No. 11/740,650, filed Apr. 26, 2007, which is a continuation of U.S. application Ser. No. 10/241,816, filed Sep. 11, 2002, which claims the benefit of U.S. provisional application Ser. No. 60/318,768, filed Sep. 11, 2001. Each of the aforementioned patent applications and patents is incorporated herein by reference. The following applications are also hereby incorporated herein by reference, but their benefit is not claimed: U.S. application Ser. No. 09/782,732, filed Feb. 13, 2001, now U.S. Pat. No. 6,780,617, which claims the benefit of U.S. provisional application Ser. No. 60/259,025, filed Dec. 29, 2000; and U.S. application Ser. No. 09/910,233, filed Jul. 20, 2001, now U.S. Pat. No. 6,748,332, which is a continuation of U.S. application Ser. No. 09/339,056, filed Jun. 23, 1999, now U.S. Pat. No. 6,318,191, which claims the benefit of U.S. provisional application Ser. No. 60/090,471, filed Jun. 24, 1998.

STATEMENT REGARDING FEDERALLY SPONSORED RESEARCH OR DEVELOPMENT

"This invention was made with government support under 1R43HL65768, 1R43HL65867 and 1R43HL67568 awarded by the National Institutes of Health. The government has certain rights in this invention." This statement is included solely to comply with 37 C.F.R. §401.14(a)(f)(4) and should not be taken as an assertion or admission that the application discloses and/or claims only one invention or that the government has rights in all subject matter disclosed and/or claimed.

BACKGROUND

Sample preparation and handling generally includes sample collection and any preprocessing required for subsequent biological and chemical assays. Sample collection and handling is an important part of in vitro diagnostic (IVD) testing, and is an important factor in determining the feasibility of test automation. With the advancement of medicine, the number of possible assays available to perform is continually increasing. In parallel, sample collection methods have evolved over the last several decades. In the case of blood sample collection, for example, disposable plastic syringes first replaced glass syringes to improve safety. Later developments had vacuum tubes replacing the traditional syringes to simplify the blood collection process. However, a vacuum tube is generally not suitable for use as an IVD test reaction chamber. Thus, a re-sampling process is necessary for delivery of the sample to distinct assay containers for each of a variety of IVD tests. Automation of these processes is a daunting task. Indeed, in large clinical testing centers giant automation testing systems costing several million dollars are currently used. The major automated task in these machines is liquid handling, which entails the pipetting of the sample from sample tubes to 96-well plates, the addition of the reagent(s) to the wells, as well as moving reaction mixtures from well to well.

Recently, nanotechnology has emerged to revolutionize automation and testing formats. In this direction, by using silicone micro-fabrication and etching technology, the lab-on-a-chip platform was developed in an attempt to integrate and miniaturize certain parts of the automation process into a chip with dimensions less than 2 mm by 2 mm. Liquid processing rates for certain lab-on-a-chip platforms can be on the scale of nanoliters per second. However, it is often difficult for users to interface with this type of platform to, for example, deliver the sample to the chip.

Another concern of current sample handling devices is the large sample volume routinely drawn from a patient for IVD testing. In the case of blood sample collection, for example, a small vacuum tube may take close to 5 ml whole blood. When multiple samples are required in the testing of various assays, several tubes of blood are frequently ordered. However, only a small amount is needed for each assay. The drawing of a large volume of blood for multiple tests is a concern for pediatric patients as it can lead to iron deficiency anemia. It is even more critical for patients with pre-existing anemia or a bleeding disorder.

SUMMARY

The present disclosure is directed to sample vessels that can permit the collection and the processing of biological and chemical samples, such as, for example, blood, saliva, tissue, or urine, in a closed system. Sample devices disclosed herein may provide a uniform sample handling system that simplifies the sample collection process and reduces exposure to biohazards. One or more of the sample vessels disclosed herein can accommodate multiple fluid samples and a plurality of assays of different types, while concomitantly reducing the volume of sample necessary for testing.

In accordance with one exemplary embodiment, a sample vessel may comprise a tubule having an opening for receiving a sample material and at least one compressible section, a generally rigid container receiving at least a portion of the tubule, and an interface in fluid communication with the opening in the tubule. The at least one compressible section may have a wall constructed at least partially from a material having sufficient flexibility to permit compression of opposed sections of the wall into contact. The interface may facilitate delivery of a sample material to the tubule through the opening.

In accordance with another exemplary embodiment, a sample vessel may comprise a tubule having a plurality of lumens and a wall constructed at least partially from a material having sufficient flexibility to permit compression of opposed sections of the wall into contact with one another, and a pressure gate connecting at least two lumens of the plurality of lumens. The pressure gate may permit selective fluid flow between the at least two lumens.

In accordance with another exemplary embodiment, a sample vessel may comprise a tubule having a wall that forms a lumen when the tubule is in an open configuration. The wall may have a plurality of sections including at least a first section of the wall having sufficient flexibility to permit compression of a portion of the tubule and at least a second section of the wall having sufficient rigidity to support a flow channel within the tubule during compression of the tubule.

In accordance with another exemplary embodiment, an apparatus for drawing a sample into a sample vessel may comprise a cylindrical housing having an opening for receiving the sample vessel, first means for compressing a first portion of the sample vessel, and second means for compressing a second portion of the sample vessel. The first compression means may be positioned at a proximal end of the housing and the second compression means may be positioned at a distal end of the housing.

BRIEF DESCRIPTION OF THE DRAWINGS

These and other features and advantages of the sample vessels disclosed herein will be more fully understood by reference to the following detailed description in conjunction with the attached drawings in which like reference numerals refer to like elements through the different views. The drawings illustrate principles of the sample vessels and methods disclosed herein and, although not to scale, show relative dimensions.

FIG. 1A is a perspective view of an exemplary embodiment of a sample vessel;

FIG. 1B is a side-elevational view in cross-section of the sample vessel of FIG. 1A;

FIG. 1C is an exploded view of the sample vessel of FIG. 1A, illustrating the tubule and collar removed from the container;

FIG. 2A is a perspective view of an exemplary embodiment of a sample vessel;

FIG. 2B is a side-elevational view in cross-section of the sample vessel of FIG. 2A;

FIG. 2C is an exploded view of the sample vessel of FIG. 2A, illustrating the tubule and collar removed from the container;

FIGS. 3A-3B are side-elevational views in cross-section of an exemplary embodiment of a sample vessel having a pair of lumens separated by a pressure gate;

FIG. 4 is a side-elevational view in cross-section of an exemplary embodiment of a sample vessel having three lumens separated by a pair of pressure gates;

FIG. 5 is a side-elevational view in cross-section of another exemplary embodiment of a sample vessel having three lumens separated by a pair of pressure gates, illustrating a self-sealing, reinforced wall section for facilitating injection by a needle;

FIG. 6A is a perspective view of an exemplary embodiment of a sample vessel having a pair of lumens connected by a micro-fluidic channel;

FIGS. 6B-6E are digital photographs of the sample vessel of FIG. 6A illustrating fluid flow through the lumens of the sample vessel;

FIG. 7A is a perspective view of an exemplary embodiment of a segmented sample vessel having a plurality of lumens;

FIGS. 7B and 7C are cross-sectional views of the sample vessel of FIG. 7A;

FIG. 8 a perspective view of another exemplary embodiment of a segmented sample vessel having a plurality of lumens, illustrating a hinged cover for the sample vessel;

FIG. 9 a perspective view of an exemplary embodiment of a segmented sample vessel having a plurality of lumens, illustrating alternative interfaces for the sample vessel;

FIG. 10A is a side elevational view in partial cross-section of an exemplary embodiment of a sample vessel, illustrating the compression of the sample vessel;

FIG. 10B is a cross-sectional view of the sample vessel of FIG. 10A taken along a line transverse to the longitudinal axis of the tubule 12;

FIGS. 11A-11C are side elevational views in cross-section of an exemplary embodiment of a sample vessel, illustrating compression of the sample vessel into a plurality of configurations;

FIG. 12 is a side elevational view in cross-section of an exemplary embodiment of a sample vessel having a composite cross-section and a micro-fluidic flow channel;

FIGS. 13A-13B are side elevational views in cross-section of another exemplary embodiment of a sample vessel having a composite cross-section and a micro-fluidic flow channel, illustrating the sample vessel in a open configuration (FIG. 13A) and a compressed configuration (FIG. 13B);

FIG. 14A is a side elevational view in cross-section of an exemplary embodiment of a sample vessel having a plurality of micro-fluidic flow channels interconnecting a plurality of depressions formed on an interior wall surface of the sample vessel;

FIG. 14B is a top view of an interior wall surface of the sample vessel of FIG. 14A;

FIGS. 15A and 15B are side elevational views in cross-section of an exemplary embodiment of a sample vessel having a composite cross-section including opposed planar wall sections, illustrating the sample vessel in an open configuration (FIG. 15A) and a compressed configuration (FIG. 15B);

FIG. 16A is a perspective view of an exemplary embodiment of a sample vessel having an adapter for facilitating handling of the sample vessel and/or connecting of the sample vessel to an external device;

FIGS. 16B-16E are side elevational views in cross-section of a plurality of exemplary embodiments of an adapter connected to the sample vessel illustrated in FIG. 16A;

FIGS. 17A-17E are perspective views of an apparatus for drawing a sample into a sample vessel, illustrating the operation of the apparatus;

DETAILED DESCRIPTION

Figure 18:
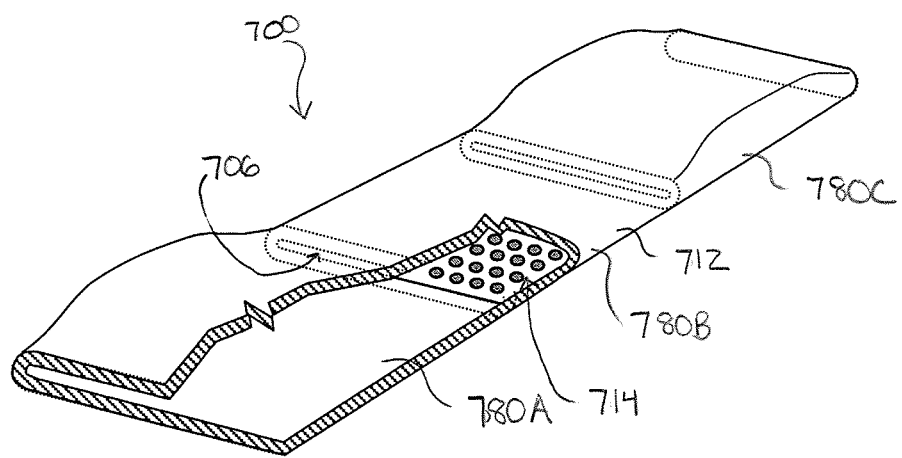
FIG. 18 is a perspective view of another exemplary embodiment of a sample vessel, illustrating the sample vessel with a portion of the wall removed to show a microarray on an interior surface of the wall of the sample vessel.

To provide an overall understanding, certain exemplary embodiments will now be described; however, it will be understood by one of ordinary skill in the art that the sample vessels and methods described herein can be adapted and modified to provide devices and methods for other suitable applications and that other additions and modifications can be made without departing from the scope of the present disclosure.

Unless otherwise specified, the exemplary embodiments described below can be understood as providing exemplary features of varying detail of certain embodiments, and therefore, unless otherwise specified, features, components, modules, and/or aspects of the exemplary embodiments can be otherwise combined, separated, interchanged, and/or rearranged without departing from the scope of the present disclosure. Additionally, the shapes and sizes of components are also exemplary and unless otherwise specified, can be altered without affecting the disclosed devices or methods.

The present disclosure is directed to sample vessels that may be utilized to collect and process one or more samples in a closed system. Exemplary samples that may be collected, processed, or otherwise contained by the sample vessels disclosed herein include biological samples, such as blood, urine, saliva, tissue, cell suspensions, microbial organisms, viruses, nucleic acids, and oligonucleotides samples; soil; water; and any other sample materials that may be assayed using known assays. The term "collection" as used herein generally refers to the extraction or gathering of the sample from a sample source, the subsequent transfer of the sample into the sample vessel, or the combination of extraction and subsequent transferring of the sample into the sample vessel. Exemplary sample gathering may include pipetting, biopsying, swabbing, drawing a fluid sample or other methods for extracting a sample from a sample source. Exemplary sample sources may include humans or other animals, plants, water sources, cell cultures, food, other sample vessels, and chemical and biological assays. Sample sources may also include interim storage media, for example, test tubes, syringes, absorbent applicators and other interim storage media for containing a sample of interest. The term "processing" as used herein generally refers to the preparation, treatment, analysis, and/or the performance of other testing protocols or assays on a content of the sample vessel in one or more steps. Exemplary processing steps include, for example: displacing a content, e.g., the sample or a reagent, of the sample vessel within the sample vessel to, for example, adjust the volume of the content, separate content components, mix contents within the sample vessel; effecting a chemical or biological reaction within a segment of the sample vessel by, for example, introducing a reagent to the sample, agitating the sample, transferring thermal energy to or from the sample, incubating the sample at a specified temperature, amplifying components of the sample, extracting, separating and/or isolating components of the sample; or analyzing the sample to determine a characteristic of the sample, such as, for example, the quantity, count, volume, mass, concentration, or expression level of a molecule, a target, a content, a marker or an analyte, binding activity, nucleic acid sequence, or nucleic acid size or other analyte size, of the sample. One skilled in the art will appreciate that the forgoing exemplary processing steps are described herein for illustrative purposes only. Other processing steps may be employed without departing from the scope of the present disclosure.

FIGS. 1A-1C illustrate an exemplary embodiment of a sample vessel 10 for collecting and processing one or more samples. The illustrated sample vessel 10 comprises a tubule 12 that provides a disposable, single use container and collection and processing vessel for the sample. The tubule 12 may be constructed from any biocompatible material and may be manufactured by injection molding, insert molding, dip molding, blow-molding, extrusion, co-extrusion, lamination, assembling from a sheet material, or other processes generally used to manufacture medical devices and implants. The tubule 12 may receive sample in solid or liquid form and, in certain embodiments, may be sized to collect and/or process sample volumes in the range of 2 microliters to 2000 microliters.

The tubule 12 may be used with any known sample testing or processing system, including, for example, the systems described in U.S. Pat. No. 6,318,191, U.S. patent application Ser. Nos. 09/339,055, and 09/782,732. Each of the aforementioned patents and patents applications is incorporated herein by reference.

In the exemplary embodiment illustrated in FIGS. 1 and 2, the tubule 12 may include an opening 14 for receiving a volume of sample material. The tubule 12 may include a compressible segment 16 having a wall 18 constructed at least partially from a material having sufficient flexibility to permit compression of the opposed segments of the wall 18 into contact. For example, the wall 18 may be constructed to converge when the compressible segment 16 of the tubule 12 is compressed in a direction perpendicular to the longitudinal axis of the tubule such that the volume of the compressed segment 16 of the tubule 12 decreases, without fracturing of the sample vessel. The walls 18 of the compressible segment 16 may be constructed of a resiliently compressible, flexible, and ultra-high strength material, such as polyethylene, polyurethane, polyvinyl chloride, polypropylene, or any other plastic material suitable for biomedical or chemical assaying applications. In one illustrative embodiment, the walls 18 of the compressible segment 16 have a wall thickness of approximately 0.01 mm to 0.5 mm. Experimental results indicate that constructing a compressible segment of a tubule having a wall thickness within this range significantly increases the efficiency of sample processing, such as heat transfer to the sample and sample transfer between the segments, and detection. In the illustrated embodiment, the compressible segment 16 of tubule 12 extends the entire length of the tubule 12. Alternatively, as discussed below, the tubule 12 may include one or more discrete compressible segment 16 spaced apart from one or more segments having different (e.g., non-flexible) properties.

In other exemplary embodiments, the tubule 12 may comprise a multi-layer wall structure. For example, the tubule 12 may include an inner layer providing bio-compatibility, using material such as polyethylene or polyurethane, and an outer layer providing lower permeability, using material such as high density polyethylene or a metal foil, such as aluminum foil or a metal deposition. One skilled in the art will appreciate that one or more additional layers may also be employed, depending on, for example, the sample type, the reagent(s) employed, and the assay(s) being performed.

The material selected to construct portions of the wall of the tubule 12, for example an optional detection segment of the tubule 12, can be optically transmissive over a selected wavelength range to facilitate optical analysis of the sample within the tubule 12.

The sample vessel 10 of the exemplary embodiment illustrated in FIGS. 1A-1C may comprise a general rigid container 20 for receiving all or at least a portion of the tubule 12. In the illustrated embodiment, the container 20 is sized to receive the complete length of the tubule 12. The container 20 may be constructed of a material having increased rigidity compared to the material of the tubule 12 to facilitate handling of the tubule 12. In certain embodiments, the container 20 may be constructed of a material having a lower permeability than the material of the tubule 12. In the illustrated embodiment, the container 20 is a glass vacuum tube. Suitable glass vacuum tubes are available under the trademark VACUTAINER® from Becton-Dickenson. The sample vessel 10 can be used in a manner similar to a glass vacuum tube to collect a sample, such as a blood sample. A container 20 may be optionally used with any of the tubule embodiments disclosed herein.

The sample vessel 10 may comprise an interface 30 that is in fluid communication with the opening 14 in the tubule 12. The interface 30 may permit collection of the sample within the tubule 12 by facilitating delivery of the sample material to the tubule 12 through the opening 14. In certain exemplary embodiments, the interface 30 may include an instrument for collecting the sample form a sample source. In the exemplary embodiment illustrated in FIGS. 1A and 1B, the interface 30 is a stopper 32 that may be coupled to the tubule 12 and may selectively seal the opening 14 in the tubule 12 to facilitate collection of the sample from a separate instrument. In the exemplary embodiment, the stopper 32 is removably and replaceably connected to the rigid container 20 and seals an opening 22 in the container 20. The stopper 32 may include a first annular portion 34 having an opening 36 sized and shaped to receive the tubule 12 in a fluid tight relationship. The first annular portion 34 is further sized and shaped to engage the walls of the container in a fluid tight relationship. The stopper 32 may include a second annular portion 38 that has a diameter greater than the diameter of both the first annular portion 34 and the container 20. The opening 36 extends through the second annular portion 38 to form an interface channel 37. A penetrable, self-sealing portion 40, such as a self-sealing membrane, may be provided to selectively seal the opening 36 and, thus, permit selective transfer of the sample (from, for example, the sample collection instrument) through the interface channel 37 into the tubule 12. The self-sealing portion 40 may be constructed of any biocompatible, resilient, self-sealing material that can be penetrated by a needle or other sample collection instrument. Suitable materials may include rubber and silicon. In certain embodiments, the stopper 32 may be constructed completely from a biocompatible, resilient, self-sealing material such as rubber or an elastomeric polymer. The interface channel 37 may taper or otherwise narrow through the cross-section of the stopper 32 to provide a guide for a needle or other instrument transferring the sample to the tubule 12.

Alternatively, the interface 30 may include other mechanisms for selectively sealing the opening 14 in the tubule 12. For example, the interface may include a self-sealing elastomeric duckbill closure. Alternatively, the interface 30 may include a valve for selectively closing and opening the interface channel 37.

The sample vessel 10 may include a clamp 50 for compressing the compressible segment 18 of the tubule to adjust the volume of the tubule 12. The clamp 50 may be configured to compress opposing wall portions of the compressible section 16 into contact thereby dividing the tubule 12 into two segments, 16A and 16B, as best illustrated in FIG. 1B. When the clamp 50 is employed, the segment 16A remains in fluid communication with the interface channel 37 and segment 16B is sealed from segment 16A by the clamp 50. Once the sample is delivered to the segment 16A of the tubule 12, the clamp 50 may be removed, providing additional volume in the tubule 12 that may permit future segmentation of the tubule and displacement of the sample within the tubule 12 by compression of the tubule 12.

The clamp 50 may be positioned at any location along the longitudinal axis of the tubule 12. Additional clamps may also be employed to divide the tubule into additional segments. In illustrated exemplary embodiment, the clamp 50 is disk-shaped and includes a radial slot 52 that is sized to receive the tubule 18 in a compressed state. One skilled in the art will appreciate that other devices may used to compress and, thereby, divide the tubule 12.

In certain exemplary embodiments, the tubule 12 may be wholly or partially evacuated to place the lumen 42 of the tubule 12 under negative pressure, e.g., at a pressure less than atmospheric pressure, to facilitate fluid flow into the tubule 12. Negative pressure can be generated by, for example, compressing the tubule 12 to collapse the lumen 42. An apparatus suitable for compressing the tubule is illustrated in FIGS. 17A-17C, described below. Alternatively the tubule 12 may be compressed by hand. The tubule 12 may also be manufactured to include a negative pressure.

In certain embodiments, the container 20 may be wholly or partially evacuated to a negative pressure. For example, the container 20 may be evacuated to inhibit loss of negative pressure within the tubule 12 and to hold the shape of the tubule 12 during storage.

A reagent may be pre-packaged in the tubule 12 or can be introduced to the tubule 12 after the sample is introduced to the tubule 12. For example, a reagent can be introduced using a reagent injector cartridge associated with the sample processing system, by a needle, or by another device capable of fluid communication with the tubule 12. The reagent can be, for example, an anticoagulant, a cell lyses reagent, a nucleotide, an enzyme, a DNA polymerase, a template DNA, an oligonucleotide, a primer, an antigen, an antibody, a dye, a marker, a molecular probe, a buffer, or a detection material. The reagent can be in liquid or solid form. In the case of a solid reagent, the reagent may be coated onto the walls of the tubule 12.

In certain exemplary embodiments, the interface 30 may include one or more chambers 44 that are in fluid communication with the tubule 12 to selectively receive a volume of fluid, such as the sample material or a reagent, from the tubule 12. In certain exemplary embodiments, he chamber 44 may be evacuated or constructed to have a substantially small initial volume and may be expendable when receiving fluid. The chamber 44 can be used as a waste container to receive and store overflow sample, wash buffer, or reaction mixture during the sample processing. For example, compressing a segment of the tubule 12 may move a portion of the sample to the chamber 44.

In the exemplary embodiment illustrated in FIGS. 2A-2C, for example, the stopper 32 includes an annular chamber 44 that is in fluid communication with the interface channel 37 in the stopper 32, and, thus, the tubule 12, through a pressure gate 48. In certain embodiments described herein, one or more pressure gates may be employed to selectively control the flow of fluid between segments, lumens, and other portions of the tubule, as well as between the tubule and external devices. For example, the illustrated pressure gate 48 provides a fluid tight seal between the chamber 44 and the interface channel 37 under normal operating conditions. The pressure gate 48 may open upon the application of a fluid pressure greater than a certain threshold pressure, for example, approximately 3 atmospheres. When a fluid pressure equal to or greater than the threshold pressure is applied to the pressure gate 48, the pressure gate 48 can open, allowing the sample or a reagent to flow from the high-pressure compartment, e.g., from the tubule 12 or from the chamber 44, to the low-pressure compartment. In certain embodiments, the pressure gate may be reversible, i.e., the pressure gate may be configured to re-close if the fluid pressure is reduced to value less than the threshold pressure. In other embodiments, the pressure gate may be irreversible, i.e., the pressure gate may be initially closed and may remain open once opened. For example, once a threshold pressure is exceeded the irreversible pressure gate remains open, even if the pressure applied to the pressure gate is reduced to below the threshold pressure. One example of an irreversible pressure gate is the pressure gate described below in connection with FIGS. 3A-3B.

In the illustrated embodiment of FIGS. 2A and 2B, the pressure gate 48 is a slit formed in the stopper 32 between the interface channel 37 and the chamber 44. The material forming the stopper 32 may be selected to be sufficiently flexible and resilient to allow the slit to open at the threshold pressure and to close at pressures lower than the threshold pressure.

A label 60 identifying the sample within the sample vessel 12 may be attached to the interface 30, the container 20, or the tubule 12. The label 60 can be a bar code or other indicia for identifying the sample.

FIGS. 3A and 3B illustrate another exemplary embodiment of a sample vessel 100. The sample vessel 100 comprises a tubule 112, which can be analogous in construction to the tubule 12, having a plurality of lumens 142A and 142B. The plurality of lumens 142A and 142B can be separated by a pressure gate 148 that permits selective fluid flow between the lumens 142A and 142B. FIG. 3A illustrates the pressure gate 148 in a closed position and FIG. 3B illustrates the pressure gate in an open position that permits fluid flow between the lumens.

In the exemplary embodiment, the lumens 142A and 142B are parallel to each other and extend in a direction generally parallel to the longitudinal axis of the tubule 12. One skilled in the art will appreciate that other lumen orientations are possible. The lumens 142A and 142B may be uniform in size (e.g., diameter, width, length) and shape or, alternatively, the lumens 142A and 142B may be different in size and shape, as in the illustrated embodiment. For example, in the illustrated embodiment, the lumen 142B has a smaller diameter than the lumen 142A. Although two lumens are illustrated in the exemplary embodiment, one skilled in the art will appreciate that the tubule 12 may be constructed of any number of lumens.

The pressure gate 148 in the present embodiment is coextensive with the lumens 142A and 142B, i.e. the pressure gate 148 extends along the entire length of the lumens. Alternatively, the pressure gate 148 may extend along only a portion or portions of the lumens, particularly in embodiments in which the tubule 12 is segmented into discrete longitudinally extending segments, as in the case of the embodiment illustrated in FIGS. 7A-7C. In such embodiments, one or more pressure gates may be provided between adjacent lumens.

In the exemplary embodiment, the opposed portions of the wall 118 of the tubule 112 are compressed into contact to form a longitudinally extending seam 170 that divides the tubule 112 into two lumens, lumens 142A and 142B. In addition to dividing the tubule 112 into multiple lumens, the seam 170 may further provide an irreversible pressure gate, pressure gate 148, between the lumens 142A and 142B. The seam 170 may be formed by mechanically clamping or otherwise compressing a cylindrical tubule or by applying vacuum pressure to the interior of a cylindrical tubule. Alternatively, the seam 170 may be formed during manufacturing of the tubule by, for example, extrusion, molding, or lamination processes. The opposed wall portions that are compressed into contact to form the seam 170, and the pressure gate 148, may be bonded together by mechanical or chemical bonding, by heating sealing, for example, by bringing hot surfaces into contact with the tubule wall immediately after extrusion, by ultrasonic welding, by mechanical interlocking, or both other connection mechanisms, to create the irreversible pressure gate 148.

The pressure gate 148 is initially in a closed configuration that inhibits fluid flow between the lumens 142A and 142B. The pressure gate 148 may open by separating the compressed opposed walls forming the pressure gate 148. Applying a threshold pressure to the pressure gate 148, as described above, may open the pressure gate 148. Alternatively, energy may be applied to the pressure gate 148 to weaken the bond between the compressed opposed walls. For example, thermal energy or light, e.g., ultra-violet light, may be applied to the pressure gate 148 or to selected portions or all of the tubule 112. The threshold pressure and/or the amount energy to open the pressure gate 148 may vary depending on the type and strength of the bond. Alternatively, the bond between the compressed opposed wall portions may be weakened or broken by chemical reaction with reagent or the sample.

In certain exemplary embodiments, one or more of the lumens may include one or more reagents. Reagents may be provided to one or more lumens prior to sample collection, e.g., one or more reagents pre-packaged with the tubule, or after sample collection. In the exemplary embodiment illustrated in FIGS. 3A and 3B, for example, a reagent may be provided in lumen 142B. Lumen 142A may be utilized for sample collection and processing. Sample collection may occur with the pressure gate 148 in a closed configuration, as illustrated in FIG. 3A. Upon transfer of the sample to lumen 142A, the pressure gate 148 may be opened automatically due to release of pressure within the lumen 142A, or selectively by applying energy to the pressure gate and/or a threshold fluid pressure. In other embodiments, the lumen 142A or 142B may be compress to provide the threshold pressure. Upon opening the pressure gate 148, the reagent(s) can mix with and interact with the sample in the lumen 142A, as illustrated in FIG. 3B. Automatic release of the pressure gate 148 and mixing of the reagent with the sample may be beneficial in certain applications, such as the mixing of an anticoagulant with a blood sample.

FIG. 4 illustrates another embodiment of a multi-lumen tubule 112 that includes three lumens, namely a first lumen 142A, a second lumen 142B, and a third lumen 142C. Each lumen may be separated a pressure gate 148, for example, an irreversible pressure gate, as described above. Each of the lumens 142A, 142B, and 142C may be provided with one or more reagents and/or may be used for sample collection and processing. For example, second lumen 142B may be provided with one or more prepackaged reagents and first lumen 142A may be used for sample collection and processing. Upon sample collection in first lumen 142A, pressure gate 148A may be opened allowing fluid communication between the second lumen 142B and the first lumen 142B. FIG. 4 illustrates the pressure gate 148A in an open configuration. Lumen 142C may be utilized as an injection channel for receiving one or more reagents, typically, but not necessarily, after sample collection in first lumen 142A. The lumen 142C may be free of sample material until pressure gate 148A is transitioned to an open configuration. FIG. 4 illustrates pressure gate 148B in a closed configuration that inhibits fluid communication between third lumen 142C and first lumen 142A. Reagent may be delivered to the third lumen 142C by a needle 190, such as a needle from a reagent injection cartridge, or by other instruments that can penetrate the lumen or otherwise provide fluid communication between a reagent source and the lumen 142C. The lumen 142C may be free of sample and reagent material until reagent is injected to avoid cross contamination of the injection needle 190. The portion of the wall 118C proximal the third lumen 142C may be constructed of a resilient, self-sealing material to facilitate re-sealing of the wall 118 after penetration to deliver reagent.

One or more lumens of the tubule 112 may include a reinforced wall portion 171, as illustrated in FIG. 5. The reinforced wall portion 171 may have an increased wall thickness compared with the remainder of the tubule wall 118 to facilitate needle penetration and re-sealing. For example, the reinforced portion may have a wall thickness of approximately 1 mm to 5 mm greater than other portions of the wall. The reinforced portion 171 may be constructed from a different material, having increased strength and/or resiliency, for example, than the remainder of the tubule wall 118. Needle guides 172 may be provided to direct needle penetration and inhibit tearing of the tubule wall 118.

FIGS. 6A-6E illustrate another exemplary embodiment of a multi-lumen tubule 112 that includes a pair of parallel lumens, namely first lumen 142A and 142B. In the illustrated embodiment, the lumens 142A and 142B are connected parallely by a thin layer fluid channel 176 in the form of a slit opening that extends the length of the tubule 112. Although one fluid channel is illustrated, additional fluid channels may be provided. The fluid channel 176 permits the sample to be moved between the first lumen 142A and the second lumen 142B and to occupy both lumens simultaneously. For example, during sample collection, portions of the sample, or the entire sample, can be transferred from the opening 114 along the length of the first lumen 142A, through the fluid channel 176, and along the length of the second lumen 142B. FIGS. 6B-6E illustrate the flow of a sample, in fluid form, through the first lumen to the end of the first lumen due to relatively low flow resistance of the lumen relative to the fluid channel 176 (FIG. 6B), through a portion 174 of the fluid channel 176 distal to the opening in the first lumen 142A (FIG. 6C), along the fluid channel 176 and through the second lumen 142B (FIG. 6D) to fill both lumens (FIG. 6D). In embodiments in which a solid reagent is packed into the lumens 142A and/or 142B of the tubule 112, flow of the sample through the lumens via the fluid channel 176 can facilitate mixing of the solid reagent with the sample. For example, in the case of blood samples, the inventors have determined that by allowing the blood sample to flow through the first lumen 142A and the second lumen 142B via the fluid channel 176 can improve mixing of the sample with an anticoagulant coated on the inner walls of the two lumens.

FIGS. 7A-7C illustrate another exemplary embodiment of a multi-lumen tubule 112 having three parallel lumens, namely a first lumen 142A, a second lumen 142B, and a third lumen 142C. In the exemplary embodiment, each lumen of the tubule 112 is divided into a plurality of longitudinally extending segments 180. For example, the third lumen 142C, illustrated in cross-section in FIG. 7B, includes five segments 180A-E. Each of the segments 180 can be used for one or more sample collection and/or sample processing steps, including the processing steps described above. In PCR (polymer chain reaction) testing, for example, one segment may used for sample collection, one segment may be used for sample pretreatment, e.g., nucleic acid extraction, one or more segments may used for sample processing, e.g., thermocycling, and one or more segments may be used for sample analysis. Any number of segments may be provided. In addition, one or more segments may be used to store reagent or as an injection channel for the delivery of reagent. The number of segments may be varied depending of the sample being processed and the processing steps selected.

Each of the segments 180 may be separated by a seal 182 that provides a temporary or permanent fluid seal between adjacent segments 180. A seal 182 may be a pressure gate, such as the reversible and irreversible pressure gates described above. Alternatively, a seal 182 may be formed by bonding or fusing of compressed opposed wall sections of the tubule. The seal 182 may be formed by applying energy, such as thermal energy or RF energy, by ultrasonic welding, or by using a bonding agent. A clamp may also be applied to the exterior of the tubule to compress the wall of the tubule and form a seal separating the segments in the tubule. For example, the clamp may be an electro-mechanical clamping mechanism as described below in connection with FIG. 10. Any other mechanism for provided an external compressive force on the tubule may be employed as the clamping mechanism. One or more clamps may be provided as part of the sample processing system used to process the sample within the tubule 112. The segments may be connected by one or more micro-fluidic flow channels that provide selective fluid connection between the segments, as described below. A seal 182 may be a filter disposed within the tubule to separate selected components of a fluid within the tubule from other segment or components of the fluid within the tubule.

In the illustrated exemplary embodiment, the interface 30 for facilitating delivery of the sample to the tubule 112 includes a needle 184 for direct collection of the sample to be processed with the sample vessel 100. The needle 184 is positioned a proximal end of the tubule and is fluid communication with an opening in the tubule 112. In the illustrated exemplary embodiment, the needle 184 is in fluid communication with an opening in the first lumen 142A, however, the needle 184 may be connected to any one or all of the lumens 142 of the tubule 112. A removable and replaceable needle cover 186 may be provided to secure the needle 184 prior to and after use. Alternatively, the needle cover 186 may be connected by a hinge, as shown in FIG. 8, or by another mechanism that allows to the cover 186 to be moved into and out of position about the needle 184. A needle safety mechanism may be coupled to the needle and the sample vessel.

FIG. 9 illustrates another embodiment of the cover 186 in which the sample collection instrument, e.g., the needle 184, is connected to the cover 186. In the illustrated exemplary embodiment, the proximal end 184A of the needle 184 may be used for sample collection from a sample source and the distal end 184B of the needle 184 may be used to provide a fluid connection with an opening in the tubule 112 through interface 30. For example, the distal end 184B may be used to penetrate a self-sealing membrane 40 provided in the interface 30. In another embodiment, a cover 190 may include a sample instrument in the form of a needle 184 and may have a compressible portion in fluid communication with the needle to facilitate drawing a fluid sample into the needle 184 and transferring the sample to the sample vessel 110. Cover 190 may be particularly useful as a finger prick for collection a blood sample.

FIG. 10 illustrates a processing station 300 of an exemplary sample processing device, such as a sample processing device described in U.S. Pat. No. 6,318,191 and U.S. patent application Ser. No. 09/782,732, filed Feb. 13, 2001. The exemplary processing station 300 includes multiple compression members, namely first compression member 302A, second compression member 302B, and third compression member 302C. Each compression member 302 is adapted to compress a sample vessel, for example, the tubule 12 of sample vessel 10 described above, and thereby displace the contents of the sample vessel, e.g. reagent or sample, within the sample vessel. Although the exemplary processing station 300 is illustrated in connection with sample vessel 10, one skilled in the art will appreciate that any of the sample vessels disclosed herein may be used in with the exemplary processing station 300. A plurality of compression members 302 may be oriented parallel to the longitudinal axis of the tubule 12, as illustrated in FIG. 10A. Alternatively, a plurality of compression members 302 may be oriented transverse to the longitudinal axis of the tubule, i.e., oriented latitudinally, as illustrated in FIG. 15B described below, or in other orientations depending on the compression configuration desired. A driver may be coupled to one or more of the compression members 302 to selectively move the compression member into contact with the sample vessel. The driver can be, for example, an electromagnetic actuating mechanism, a motor, a solenoid, or any other device for imparting motion on the compression members 302. A stationary member 304 or another compression member may be provided opposite compression member 302.

A compression member 302 may be employed to compress a portion of the wall 18 of the tubule 12 into contact with another portion of the wall 118 of the tubule 12 to form a seal in the tubule 12 and thereby divide the tubule 12 into multiple segments. In alternative embodiments, a compression member 302 may compress a portion of the wall 18 of the tubule 12 into proximity with another portion of the wall 18 of the tubule 12 to form a micro-fluidic channel 306 between segments of the tubule 12. For example, in the embodiment illustrated in FIG. 10, compression member 302B compresses a portion of wall 18 into proximity with another portion of the wall to create a micro-fluidic channel 306 that connects a first segment 180A and a second segment 180B of the tubule 12. The width of the micro-fluid channel 306 may be adjusted by displacing the compression member 302B towards or away from the tubule 12. Micro-fluid channels may be formed having a gap less than 200 microns, preferably 10 to 30 microns.

The compression members 302 may be arranged in a variety of orientations to compress the tubule 12 into a variety of configurations. For example, in FIG. 10B, the width of the micro-fluidic channel 306 extends across the entire width of the tubule 12. Such a compressed configuration may be formed by a compression member 302B having a planar compression surface 308 for engaging the tubule 12 that is sized to engage the entire compressed wall surface of the tubule. In other embodiments, the size or shape of the compression surface 308 may be varied and the number and orientation of compression members 302B may be varied. For example, FIG. 11A illustrates a compressed tubule 12 having a centrally located flow channel 306 that may be formed by a compression member 302 having a groove formed on the bottom surface thereof or by three compression members 302 aligned transverse to the longitudinal axis of the tubule 12. A centrally positioned compression member may compress wall portion 18A into proximity with an opposed wall portion, while a pair of compression members, one on either side of the central compression member, may compress side wall portions 18B and 18C, respectively. FIG. 11B illustrates a compressed tubule 12 having a centrally located lumen 306 formed by compressing the tubule 12 into a non-planar configuration. In this illustrated embodiment, a triangular profile flow channel is formed, which inherently forces a cell or particle to flow through the central line of the channel, thus reducing the need to regulate the tolerance in forming the flow channel. FIG. 11C illustrates a compressed tubule 12 having a flow channel 306 formed off-set from the center of the tubule 12. In the illustrated embodiment, the flow channel is formed on a lateral edge of the tubule 12.

At least a portion of the wall of the tubule 12 may be optically transparent to allow monitoring or detection of the sample or reaction. The transparent portion of the wall may be located in the flow channel section, thus allowing the monitoring of sample or reaction under flow or through a thin layer of liquid, for processes such as counting cells, reaction hybridization, or detection, for example, microarray spots.

One skilled in the art will appreciate that while it may be desirable in certain applications for the wall of the tubules disclosed herein to be uniform along the circumference and the longitudinal axis of the tubule, only a portion of the wall along the circumference and/or longitudinal axis of the tubule need be resilient and compressible. Thus, the tubule need not have a uniform cross-section, either along the longitudinal axis or transverse to the longitudinal axis. In certain exemplary embodiments, for example, a section of the wall of the tubule may be formed of a material selected to provide a property distinct from a property of another section of the wall. Exemplary properties that may be varied include permeability, flexibility, hardness, resiliency, optical transparency, biocompatibility, surface smoothness of the inner wall, and surface chemistry of the inner wall, for example the hydrophobic or hydrophilic properties of the inner wall surface. Surface properties may be rendered by coating with a layer of material, such as a thermoset urethane aired by UV energy or other cross linking methods.

FIGS. 15A and 15B illustrate an exemplary embodiment of a sample vessel 10 in the form of a tubule 12 having wall sections 18A that are formed of a material selected to provide a property distinct from a property of a plurality of other wall sections 18B of the tubule 12. Wall sections 18A may be opposed to one another, as illustrated, or positioned at other positions in the cross section of the tubule 12. Wall sections 18A may similar in size, shape and material properties, as illustrated, or may vary in size, shape, and material properties from one another. In the illustrated embodiment, wall sections 18A are selected from a material having sufficient flexibility to permit compression of the tubule 12, as illustrated in FIG. 15B. Wall sections 18B are formed of a material having increased rigidity compared to the material of wall sections 18A. In the illustrated embodiment, wall sections 18B preferably have sufficient rigidity to resist flexing during compression and thereby maintain a planar configuration. Wall sections 18B may be opposed to one another, as illustrated, or positioned at other positions in the cross section of the tubule 12. Wall sections 18B may be similar in size, shape and material properties, as illustrated, or may vary in size, shape, and material properties from one another. In the illustrated embodiment, the wall sections 18A and 18B are spaced latitudinally, i.e., about the circumference of the tubule 12 and transverse to the longitudinal axis. Wall sections 18A and 18B are interposed between one another in an alternating arrangement about the circumference of the tubule 12. Wall sections 18A and 18B may be formed from the same material or a different material. For example, wall sections 18A may be formed of a relatively low durometer polyurethane, for example, in the range of from 40 A to 90 A depending on thickness, and wall sections 18B may be formed of a polyurethane having a relatively higher durometer, for example, in the range of from 40 D to 90 D depending on thickness. A tubule having wall sections of varying properties may be manufactured by conventional extrusion, co-extrusion, injection molding, insert molding, dip molding, blow molding, transfer molding, or lamination processes.

During compression of the tubule 12 illustrated in FIGS. 15A and 15B, the wall sections 18A flex allowing a first wall section 18B to be moved into proximity or contact with second wall section 18B'. Wall sections 18B may provide improved sealing surfaces due to the increased rigidity compared with wall sections 18A. In addition, walls sections 18B permit the formation of a precisely defined micro-fluid flow channel 306, as illustrated in FIG. 15B. The increased rigidity of the wall sections 18B allows for the formation of a smaller and more uniform flow channel than more flexible wall sections. FIG. 15B illustrates the formation of a micro-fluidic flow channel 306 between segments 180A and 180B of the tubule 12. In the illustrated embodiment, the compression members 302A-C are oriented transverse to the longitudinal axis of the tubule to form a flow channel 306 that extends latitudinally, i.e., transverse to the longitudinal axis, between first segment 180A and second segment 180B.

In other exemplary embodiments, the number of wall sections of differing properties may be varied. For example, a single wall section 18B having increased rigidity may be provided or three or more wall sections having increased rigidity may be provided.

In certain exemplary embodiments, a flow channel 306 may be pre-formed in a section of the wall 18 of the tubule as illustrated in FIGS. 12 and 13A-B. The pre-formed flow channel 306 may be a grove 316 formed in a wall section of the tubule 12. The groove 316 may be formed by scoring or etching the wall 18 of the tubule 12 or may be formed during the extrusion or molding of the tubule 12. The groove 316 in the illustrated embodiments extends longitudinally, however, the groove 316 may be formed in any direction, including latitudinally. More than one groove 316 may be provided. The groove 316 may have a variety of cross-section shapes and sizes. In the embodiment illustrated in FIG. 12, the groove 316 has a triangular cross-section. In the embodiment illustrated in FIGS. 13A-13B, the groove 316 has a rectangular cross-section. The cross-sectional size of the groove 316 can be selected based on desired shear rate profile of the flow channel 306.

The groove 316 may be formed in any section of the wall 18 of the tubule 12. For example, the groove 316 may be formed in a wall section 18B having increased rigidity compared to other wall sections of the tubule 12, as is the case for the illustrated embodiments of FIGS. 12 and 13A-B. During compression of the tubule 12, as illustrated in FIG. 13B, the wall section 18B contacts wall section 18B' to provide a fluid tight seal. Groove 316 provides a flow channel 306 that extends longitudinally through the fluid tight seal.

FIGS. 14A and 14B illustrate an exemplary embodiment of a sample vessel 400 comprising a tubule 412 having a plurality of flow channels 306 and one or a plurality of depressions 408 formed on an interior wall surface 410 of the wall 418 of the tubule 412. Each depression 408 can form a micro-cup during compression of the tubule 412 that can hold a fixed volume of sample or reagent. The volume of a depression forming a micro-cup can be from 0.1 microliter to 10 microliter, preferably, from 0.5 microliter to 4 microliter. A pattern of one or more grooves 316 and depressions 408 may be formed on the interior wall surface 410 of the tubule 412 and may interconnect to provide a network of micro-cups interconnected by micro-fluidic flow channels 306, as best illustrated in FIG. 14B. Such a network may be used to perform a variety of processing steps within one or more micro-cups and may permit the transport of small, precise volumes of sample and reagent between the micro-cups via micro-fluid flow channels by selectively compressing the tubule 412. The network of grooves and depressions may be formed using semi-conductor processing techniques. For example, a mask pattern may be applied to an interior wall surface of the tubule 12 using conventional photolithographic techniques. The grooves and depressions may then be formed by etching or otherwise removing portions of the interior wall surface based on the pattern imaged onto the interior wall surface. It may be desirable to form the network of grooves and depressions on a planar substrate 418A constructed of a material suitable for use in the tubule 412, as illustrated in FIGS. 14A and 14B. A second layer 418B of material can be attached to the planar substrate 418A to form the wall 418 of the tubule 412.

Referring to FIGS. 14A and 14B, one or more sample or reagent processing devices 414 may be provided on the interior wall surface 410 of the tubule 412. For example, a microarray device may be embedded on the interior wall surface 410 of the tubule 412. An exemplary microarray device 414 may comprise a plurality of reagent coated zones for simultaneous analysis of a plurality of analytes within a sample. The processing device 414 may also be a micro-fluid device or a lab-on-a-chip device, or any other device for processing a sample. The processing device 414 may be interconnected with one or more depressions 408 or other processing devices via flow channels 306. Any number of processing devices of any type may be provided in the tubule 412.

Referring to FIG. 18, a sample vessel 700 comprising a tubule 712 divided into multiple segments 780A-C. Segment 780B may be constructed of a rigid, generally non-flexible material and may have a processing device, such as a microarray 714, embedded on the interior wall thereof. The segment 780B may provide a pre-formed flow channel between two compressible segments 780A and 780C. By alternately compressing the two flexible segments 708A and 780C, the sample may flow through the flow channel 706 to facilitate high efficient hybridization or binding of analytes to the reagent spots of the microarray 714. A flow channel 706 having a small gap may also increase wash efficiency as a laminar flow is formed.

FIGS. 16A-16E illustrates an exemplary embodiment of a sample vessel 10 comprising a tubule 12 and an adapter 500 that is connected to the tubule 12 of the sample vessel 10. The adapter 500 may be provided to facilitate handling of the sample vessel 10 and/or to facilitate connection of the tubule 12 to an external device, such as a micro-fluid device, a lab-on-a-chip device, a microarray device, a reagent source, another sample vessel, or any other device suitable for containing or processing a sample. In the illustrated embodiments, the adapter 500 is a generally planar tab that is coextensive with the tubule 12. One skilled in the art will appreciate that the adapter 500 need not be coextensive with the tubule and may be constructed of varying sizes and shapes depending upon the application. Moreover, more than one adapter may be provided.

The adapter 500 may be constructed of any material suitable for use in construction the tubule 12. For example, the adapter may be constructed of polyurethane. The adapter 500 may be constructed of the same or a different material than the tubule 12. To facilitate handling, the adapter 500 may be constructed of a material having increased rigidity compared to the material of the tubule 12, for example a high durometer polyurethane. In certain embodiments, the adapter 500 may be manufactured with the tubule 12 in, for example, a coextrusion process or an injection molding process. Alternatively, the adapter 500 may be manufactured independently and attached to the tubule 12 in a post-forming process by, for example, bonding.

The exemplary embodiment of FIGS. 16A-16E also includes a container 20 and an interface 30, as described above. The container 20 removably and replaceably encloses the tubule 12 to protect the sample tubule 12 and when removed, may allow direct manipulation of tubule 12. A portion of adapter 500 may not be enclosed by container 20. The exposed portion of the adapter 500 can be directly accessed by a user for labeling, handling and other processing. The interface 30 includes an interface channel 37 that communicates with an opening in the tubule 12 to facilitate delivery of a sample to the tubule 12. In the illustrated embodiment, a removable and replaceable cover 586 is provided to selectively open and close the interface channel 37. The exemplary cover 586 includes a sample collection instrument in the form of a tissue swab 584 for collecting tissue samples from a sample source.

FIGS. 16A-B illustrate an embodiment of the adapter 500 that is constructed to facilitate handling of the sample vessel 10.

FIG. 16C illustrates an embodiment of the adapter 500C that is designed to facilitate delivery of a reagent or a sample from an external device, such as a needle 90 from a reagent injector cartridge. The adapter 500C includes a reversible or irreversible pressure gate 48 that provides a fluid channel to permit selective displacement of a fluid, e.g., a sample or reagent, between the tubule 12 and the external device, in the present embodiment, needle 90. The adapter 500C may include a self-sealing membrane 540, valve, or other sealing mechanism to facilitate selective communication with the external device. A reservoir 502 may be provide to contain a fluid delivered from the external device or fluid from the tubule 12. In use, the needle 90 may penetrate the self-sealing membrane 540 to deliver fluid to the reservoir 502 or to withdraw fluid from the reservoir 502. Pressure gate 48 may be opened in the manner described above, e.g. by compressing the tubule 12 or the reservoir 502, to withdraw fluid from the reservoir 502 or to deliver fluid to the reservoir 502 from the tubule 12. The needle 90 may be coupled with a sensor, such as an electrode, a fiber optical sensor, for penetrating the self sealing membrane 540 and measuring a sample property.

FIG. 16D illustrates an embodiment of the adapter 500D that comprises a compressible reservoir 506 and a reversible or irreversible pressure gate 48 that provides a fluid channel to permit selective displacement of a fluid, e.g., a sample or reagent, to the tubule 12 from the compressible reservoir 506.

The compressible reservoir 506 may contain a pre-packed reagent. In certain embodiments, the compressible reservoir 506 may be a blister pack. Upon compression of the compressible reservoir 506, pressure gate 48 may open and fluid with the compressible reservoir 506 can be displaced in to the tubule 12.

FIG. 16E illustrates an embodiment of the adapter 500E that comprises a reservoir 502, a first reversible or irreversible pressure gate 48A that provides a fluid channel to permit selective displacement of a fluid, e.g., a sample or reagent, between the tubule 12 and the reservoir 502, and a second reversible or irreversible pressure gate 48B that provides a fluid channel to permit selective displacement of a fluid, e.g., a sample or reagent, between an external device 508 and the reservoir 502. A connector 509 may be provided to interface with the external device 508. Such device may be an Access™ card for Micronics Inc., a LabChip® product from Caliper, Inc. or a GeneChip® from Affymetrix, Inc.

FIGS. 17A-E illustrate another exemplary embodiment of a sample vessel 600 that comprises a tubule 10 and an apparatus 602 for drawing a sample into the tubule 12 of the sample vessel 10. The apparatus 602 includes a cylindrical housing 604 having an opening 606 for receiving the tubule 12. The opening 602 extends from a proximal end 608 to a distal end 610 of the housing 604. Both the housing 604 and the opening 606 can be sized and shaped to accommodate the size and shape of the tubule 12 or other sample vessels. For example, the housing 604 and opening 606 are cylindrical in shape and have a circular cross-section analogous to that of the tubule 12. The adapter 600 comprises first means 612 for compressing a first portion of the tubule 12 and second means 614 for compressing a second portion of the tubule 12. The first compression means 612 may be spaced apart from the second compression means 614. For example, the first compression means 612 may be positioned at the proximal end 608 of the housing 602 and the second compression means 614 may be positioned at the distal end 610 of the housing 602. The spacing between the first and second compression means may be selected based on the desired sample collection volume in the tubule 12.

The first compression means 612 may comprise a first pair of spaced apart rollers, 616A and 616B. At least one of the rollers 616A-B may be selectively movable into contact with the other roller to compress the tubule 12 between the rollers 616A-B. A first activator 620 may be coupled to the rollers 616A, 616B to effect separation or compression of the rollers. The second compression means 612 may comprise a second pair of spaced apart rollers, 618A and 618B. At least one of the rollers 618A-B may be selectively movable into contact with the other roller to compress the tubule 12 between the rollers 618A-B. A second activator 622 may be coupled to the rollers 618A, 618B to effect separation or compression of the rollers. In addition to rollers, or other compression mechanisms may be employed for the first and second compression means, including the compression members described above. Any structure suitable for selective compression of the tubule 12 may be employed. The first and second compression means need not be the same structure.

In use, the tubule 12 is inserted into the opening 606 at the proximal end 608 of the housing 604 and drawn completely through the opening 606 to the distal end 610 of the housing 604. As the tubule 12 is drawn through the housing 604, the tubule 12 is flatten and compressed, as illustrated in FIG. 17B, to evacuate the tubule 12. At the time of sample collection, a cover 686 may be removed to expose a sample collection instrument, such as a needle 684, that is in fluid connection with the tubule 12. The needle 684 can be inserted into the sample source and the first compression means 612 may be separated to draw the sample into the tubule 12, as illustrated in FIG. 17C. The sample vessel 10 may then be inserted into a device 630 for removing the needle 684, or other sample collection instrument, as illustrated in FIG. 17D. The device 630 may also include a mechanism for sealing the proximal end of the tubule 12 after the needle 684 is removed, by, for example, compressing and heating the wall of the tubule 12 at the proximal end to bond or fuse the walls together. The second compression means 614 may separate and the adapter 600 may be removed from the tubule 12, as illustrated in FIG. 17E.

While the sample vessels disclosed herein have been particularly shown and described with references to exemplary embodiments thereof, it will be understood by those skilled in the art that various changes in form and details may be made therein without departing from the spirit and scope of the disclosure. Those skilled in the art will recognize or be able to ascertain using no more than routine experimentation, many equivalents to the exemplary embodiments described specifically herein. Such equivalents are intended to be encompassed in the scope of the present disclosure.

What is claimed is:

1. A sample vessel, comprising:
    a segmented tubule with walls that oppose one another having an opening for receiving a sample material,
    at least one compressible section, the at least one compressible section having a wall constructed at least partially from a material having sufficient flexibility to permit compression of opposed sections of the wall into contact with one another, and
    at least two segments of the tubule being fluidically isolated from one another by a fluid-tight seal between opposed sections of the tubule wall bonded to one another, wherein said fluid-tight seal is an irreversible pressure gate which irreversibly opens upon application of fluid pressure greater than a threshold value to permit selective fluid communication between the opposed sections; and
    an interface in fluid communication with the opening of the tubule,
    wherein the sample vessel further comprises an adapter attached to the tubule, the adapter having increased rigidity compared to the tubule, and
    wherein the adapter comprises a generally planar tab.

2. The sample vessel of claim 1, further comprising at least one reagent contained within a segment of the tubule, the reagent being separated from other reagents or sample by fluid-tight seal.

3. The sample vessel of claim 1, further comprising a generally rigid container receiving at least a portion of the tubule.

4. The sample vessel of claim 1, wherein the adapter comprises a ring to which the tubule is attached at the tubule opening.

5. The sample vessel of claim 1, wherein the adapter facilitates connection of the sample vessel to an external device.

6. The sample vessel of claim 1, wherein the adapter coextensive with the tubule.

7. The sample vessel of claim 1, wherein the tubule comprises a plurality of layers, and wherein a first layer having a first permeability and a second layer exterior to the first layer and having a second permeability lesser than the first permeability.

8. The sample vessel of claim 7, wherein the second layer is constructed of a metal foil.

9. The sample vessel of claim 1, wherein the tubule comprises a plurality of lumens aligned in parallel along the tubule.

10. The sample vessel of claim 9, wherein at least one lumen is of a different size or shape than another lumen of the plurality of lumens.

11. The sample vessel of claim 9, further comprising a pressure gate between two lumens of the plurality of lumens to permit selective fluid communication between the two lumens.

12. The sample vessel of claim 9, wherein opposed portions of the wall of the tubule are shaped into contact to form a longitudinally extending seam that divides the tubule into at least two lumens that extend generally parallel to a longitudinal axis of the sample vessel.

13. The sample vessel of claim 1, further comprising at least one groove formed in a wall of the tubule, the at least one groove forming at least one of a micro-fluidic channel, a fixed volume micro-cup, or a combination thereof.

14. The sample vessel of claim 1, wherein the interface includes a chamber in fluid communication with the tubule for selectively receiving a volume of sample material and/or reagent from the tubule.

15. The sample vessel of claim 1, further comprising a removable and replaceable cover to selectively open and close the interface.

16. The sample vessel of claim 1, further comprising a seal-sealing injection channel, the injection channel being normally substantially free of sample material and capable of fluid communication with the tubule.

17. The sample vessel of claim 1, further comprising a microarray device embedded on an interior wall surface of the tubule, the microarray having a plurality of reagent coated zones for simultaneous analysis of a plurality of analytes.

18. The sample vessel of claim 1, further comprising a filter disposed within the tubule to separate selected components of a fluid within the tubule from other components of the fluid within the tubule.

19. The sample vessel of claim 1, wherein the interface includes an instrument for obtaining a sample.

20. The sample vessel of claim 1, wherein a portion of the tubule is at least partially evacuated.

21. The sample vessel of claim 1, wherein at least a portion of the wall of the tubule is coated with a layer of material to provide a surface property to the wall.

22. The sample vessel of claim 1, further comprising at least one additional tubule, the tubules arranged to form a row.

23. The sample vessel of claim 1, wherein the fluid-tight seal that irreversibly opens upon application of fluid pressure greater than a threshold value spans the tubule's width.

24. The sample vessel of claim 23, which comprises a linear contiguous array of compressible segments along the vessel, each spanning the tubule's width, and each fluidically isolated from an adjacent segment by a fluid-tight seal, formed by a bonding between opposed sections of the tubule wall, that irreversibly opens upon application of fluid pressure greater than a threshold value and that spans the tubule's width.

\* \* \* \* \*